United States Patent
Kadoury et al.

(10) Patent No.: US 11,798,229 B2
(45) Date of Patent: Oct. 24, 2023

(54) INTERVERTEBRAL DISC MODELING

(71) Applicant: NuVasive, Inc., San Diego, CA (US)

(72) Inventors: Samuel Kadoury, San Diego, CA (US); Eric Finley, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 17/519,164

(22) Filed: Nov. 4, 2021

(65) Prior Publication Data
US 2022/0058869 A1 Feb. 24, 2022

Related U.S. Application Data

(63) Continuation of application No. 16/852,516, filed on Apr. 19, 2020, now Pat. No. 11,276,232, which is a (Continued)

(51) Int. Cl.
*G06T 15/00* (2011.01)
*G06T 17/20* (2006.01)
(Continued)

(52) U.S. Cl.
CPC ............. *G06T 17/20* (2013.01); *A61B 5/055* (2013.01); *A61B 5/4566* (2013.01); *G06N 3/045* (2023.01); *G06N 3/08* (2013.01); *G06T 7/0012* (2013.01); *G06T 7/11* (2017.01); *A61B 2576/02* (2013.01); *G06T 2207/10088* (2013.01);
(Continued)

(58) Field of Classification Search
USPC ........................................................ 345/418
See application file for complete search history.

(56) References Cited

U.S. PATENT DOCUMENTS 9,214,028 B2 12/2015 Feilkas
9,875,540 B2 1/2018 Blumhofer
(Continued)

FOREIGN PATENT DOCUMENTS

CN 108399616 8/2018
JP 2009207727 9/2009
(Continued)

OTHER PUBLICATIONS

Haq R, Aras R, Besachio DA, Borgie RC, Audette MA. 3D lumbar spine intervertebral disc segmentation and compression simulation from MRI using shape-aware models. International journal of computer assisted radiology and surgery. Jan. 2015; 10(1): 45-54.*
(Continued)

*Primary Examiner* — Phu K Nguyen
(74) *Attorney, Agent, or Firm* — Merchant & Gould P.C.

(57) ABSTRACT

A method is disclosed for spinal anatomy segmentation. In one example, the method includes combining a fully convolutional network with a residual neural network. The method also includes training the combined fully convolutional network with the residual neural network from end to end. The method also includes receiving at least one medical image of a spinal anatomy. The method also includes applying the fully convolutional network with the residual neural network to at least one medical image and segmenting at least one vertebral body from the at least one medical image of the spinal anatomy.

17 Claims, 4 Drawing Sheets

Related U.S. Application Data continuation of application No. PCT/US2018/056797, filed on Oct. 19, 2018.

(60) Provisional application No. 62/575,260, filed on Oct. 20, 2017.

(51) Int. Cl.

| | |
|---|---|
| *G06T 7/11* | (2017.01) |
| *A61B 5/055* | (2006.01) |
| *A61B 5/00* | (2006.01) |
| *G06N 3/08* | (2023.01) |
| *G06T 7/00* | (2017.01) |
| *G06N 3/045* | (2023.01) |

(52) U.S. Cl.
CPC .............. *G06T 2207/20081* (2013.01); *G06T 2207/20084* (2013.01); *G06T 2207/30012* (2013.01)

(56) References Cited

U.S. PATENT DOCUMENTS

| | | | |
|---|---|---|---|
| 11,276,232 B2* | 3/2022 | Kadoury | .................. G06T 7/11 |
| 2016/0300026 A1 | 10/2016 | Bogoni et al. | |
| 2019/0069882 A1 | 3/2019 | Moctezuma De La Barrera | |
| 2022/0058869 A1* | 2/2022 | Kadoury | .............. A61B 5/4566 |

FOREIGN PATENT DOCUMENTS

| | | |
|---|---|---|
| JP | 2014158628 | 9/2014 |
| JP | 2016119954 | 7/2016 |
| JP | 2017-158781 | 9/2017 |
| WO | 2017/106645 | 6/2017 |

OTHER PUBLICATIONS

Abdi M, Nahavandi S. Multi-residual networks: Improving the speed and accuracy of residual networks. arXiv preprint arXiv:1609.05672. Sep. 19, 2016.

Castro AP, Lacroix D. Computational modelling of the intervertebral disc: A case-study for biomedical composites. Biomedical Composites. Jan. 1, 2017 :479-500.

Chen et al., "3D Fully Convolutional Networks for Intervertebral Disc Localization and Segmentation", MIA 2016, LNCS 9805, pp. 375-382 (2016).

Fallah Faezeh et al: IIA novel objective function based on a generalized kelly criterion for deep learning. 2017 Signal Processing: Algorithms, Architectures, Arrangements, and Applications (SPA), Division of Signal Processing and Electronic Systems. Poznan University of Technology, Sep. 20, 2017 (Sep. 20, 2017). pp. 84-89. XP033276612. DOI: 10.23919/SPA.2017.8166843.

Gholipour & Arjmand, Artificial Neural Networks to Predict 3D Spinal Posture in Reaching and Lifting Activities; Applications in Biomechanical Models, Journal of Biomechanics 49 2946-2952 (2016).

Jamaludin Amir et al: 11 ISSLS Prize in Bioengineering Science 2017: Automation of magnetic resonance images (MRIs) of the lumbar spine without human intervention is comparable with an expert radiologist . European Spine Journal. Springer Verlag, Berlin, DE, vol. 26. No. 5. Feb. 6, 2017 (Feb. 6, 2017), pp. 1374-1383. XP036222640. ISSN: 0940-6719. DOI: 10.1007/S00586-017-4956-3.

Ji et al., "Automated intervertebral disc segmentation using deep convolutional neural networks", in CSI 2016 : Proceedings of the International Workshop on Computational Methods and Clinical Applications for Spine Imaging, Springer, Cham, Switzerland, pp. 38-48, doi: 10.1007/978-3-319-55050-3_4.

Korez Robert et al: Determination of intervertebral disc space from CT images of the lumbar spine 11 • Progress in Biomedical Optics and Imaging. SPIE—International Society for Optical Engineering. Bellingham. WA. US. vol. 9034. Mar. 21, 2014 (Mar. 21, 2014). pp. 90342Q-90342Q. XP060031767. ISSN: 1605-7422. DOI: 10.1117/12.2043734 ISBN: 978-1-5106-0027-0.

Labao, Alfonso, and Pros Naval. "Non-motion-based segmentation of fish objects in underwater videos using resnet-fcn." In Asian Conference on Intelligent Information and Database Systems. Feb. 2017.

Shakeri et al. "Inter-vertebral disc modelling from pairs of segmented vertebral models using trainable pre-processing networks", 2018 IEEE 15th International Symposium on Biomedical Imaging (2018).

Xu Z, Wang J, Xu P, Liu T. Infrared Image Temperature Measurement Based on FCN and Residual Network. In Chinese Intelligent Systems Conference Oct. 14, 2017 (pp. 769-775). Springer, Singapore.

Japanese Notice of Rejection in Application 2020-521914, dated Oct. 4, 2022, pages.

PCT Intnernation Preliminary Report on Patentability in International Application PCT/US2018/056797, dated Apr. 30, 2020, 10 pages.

PCT Intnernation Search Report and Written Opinion in International Application PCT/US2018/056797, dated Jan. 29, 2019, 12 pages.

Faezeh, Falleh et al., "A novel objective function based on a generalized kelly criterion for deep learning", 2017 Signal Processing: Algorithms, Architectures, Arrangements, and Applications (SPA), IEEE 2017, pp. 84-89.

Jamaludin, Amir et al., "Automation of reading of radiological features from magnetic resonance images (MRIs) of the lumbar spine without human intervention is comparable with an expert radiologist", Eur. Spine J., 2017, vol. 26, pp. 1374-1383.

Korez, Robert et al., "Determination of the intervertebral disc space from CT images of the lumbar spine", Abstract, Medical Imaging 2014, Image Processing; 9034 2Q, 2014, Proc. vol. 9034, pp. 1-6.

European Search Repoer in Application 21170454.9, dated Jul. 8, 2021, 11 pages.

* cited by examiner

| Layer Name | Block Type | Output Resolution | Output Width | Repetition Number |
|---|---|---|---|---|
| Down 1 | Conv 3 x 3 | 512 x 512 | 32 | 1 |
| Down 2 | Simple block | 256 x 256 | 32 | 2 |
| Down 3 | Basic block | 128 x 128 | 128 | 1 |
| Down 4 | Basic block | 64 x 64 | 256 | 1 |
| Down 5 | Basic block | 32 x 32 | 512 | 1 |
| Across | Bottleneck | 32 x 32 | 1024 | 1 |
| Up 1 | Basic block | 64 x 64 | 512 | 1 |
| Up 2 | Basic block | 128 x 128 | 256 | 1 |
| Up 3 | Basic block | 256 x 256 | 128 | 1 |
| Up 4 | Simple Block | 512 x 512 | 32 | 2 |
| Up 5 | Conv 3 x 3 | 512 x 512 | 32 | 1 |
| Classifier | Conv 1 x 1 | 512 x 512 | 1 | 1 |

Figure 2

INTERVERTEBRAL DISC MODELING

CROSS-REFERENCE TO RELATED APPLICATION

This application is a continuation of U.S. patent application Ser. No. 16/852,516, filed Apr. 19, 2020, which is a continuation of International Application PCT/US18/56797, filed on Oct. 19, 2018, currently pending, which claims priority to U.S. Provisional Application No. 62/575,260, filed on Oct. 20, 2017, now expired, the entire disclosures of which are incorporated herein by reference.

BACKGROUND

This disclosure relates to a method of modeling intervertebral discs. Accurate segmentation of vertebrae from medical images is an important preliminary task in image-guided spine surgery. Describing the detailed shape of the vertebrae can considerably help with the early diagnosis, surgical planning, and follow-up assessment of a number of spinal disorders. In recent years, magnetic resonance imaging (MRI) has become a valuable, non-invasive tool for vertebral analysis. Unlike computed tomography (CT), MRI does not pose risks associated with exposure to radiation. However, magnetic resonance image analysis encounters several challenges for segmentation, such as variability in resolutions and intensity ranges across different scans.

SUMMARY

The needs above, as well as others, are addressed by embodiments of methods for modeling intervertebral discs as described in this disclosure.

A method is disclosed for spinal anatomy segmentation. The method includes combining a fully convolutional network with a residual neural network. The method also includes training the combined fully convolutional network with the residual neural network from end to end. The method also includes receiving at least one medical image of a spinal anatomy. The method also includes applying the fully convolutional network with the residual neural network to the at least one medical image and segmenting at least one vertebral body from the at least one medical image of the spinal anatomy.

Another method is disclosed for spinal anatomy segmentation. The method includes combining a fully convolutional network with a residual neural network. The method also includes training the combined fully convolutional network with the residual neural network from end to end. The method also includes receiving at least one magnetic resonance image of a spinal anatomy. The method also includes applying the fully convolutional network with the residual neural network to the received at least one magnetic resonance image and segmenting at least one vertebral body from the at least one magnetic resonance image of the spinal anatomy. The method also includes extracting from the segmented at least one magnetic resonance image (i) a first three-dimensional vertebral surface that corresponds to a top vertebra and (ii) a second three-dimensional vertebral surface that corresponds to a lower vertebra, wherein the lower vertebra is adjacent to the top vertebra. The method also includes modeling an intervertebral disc mesh based on a surface reconstruction that includes the first three-dimensional vertebral surface and the second three-dimensional vertebral surface.

DESCRIPTION OF THE FIGURES

FIG. 2 depicts an example architecture of a residual neural network, according to an embodiment of the present disclosure.

DETAILED DESCRIPTION

Figure 1:
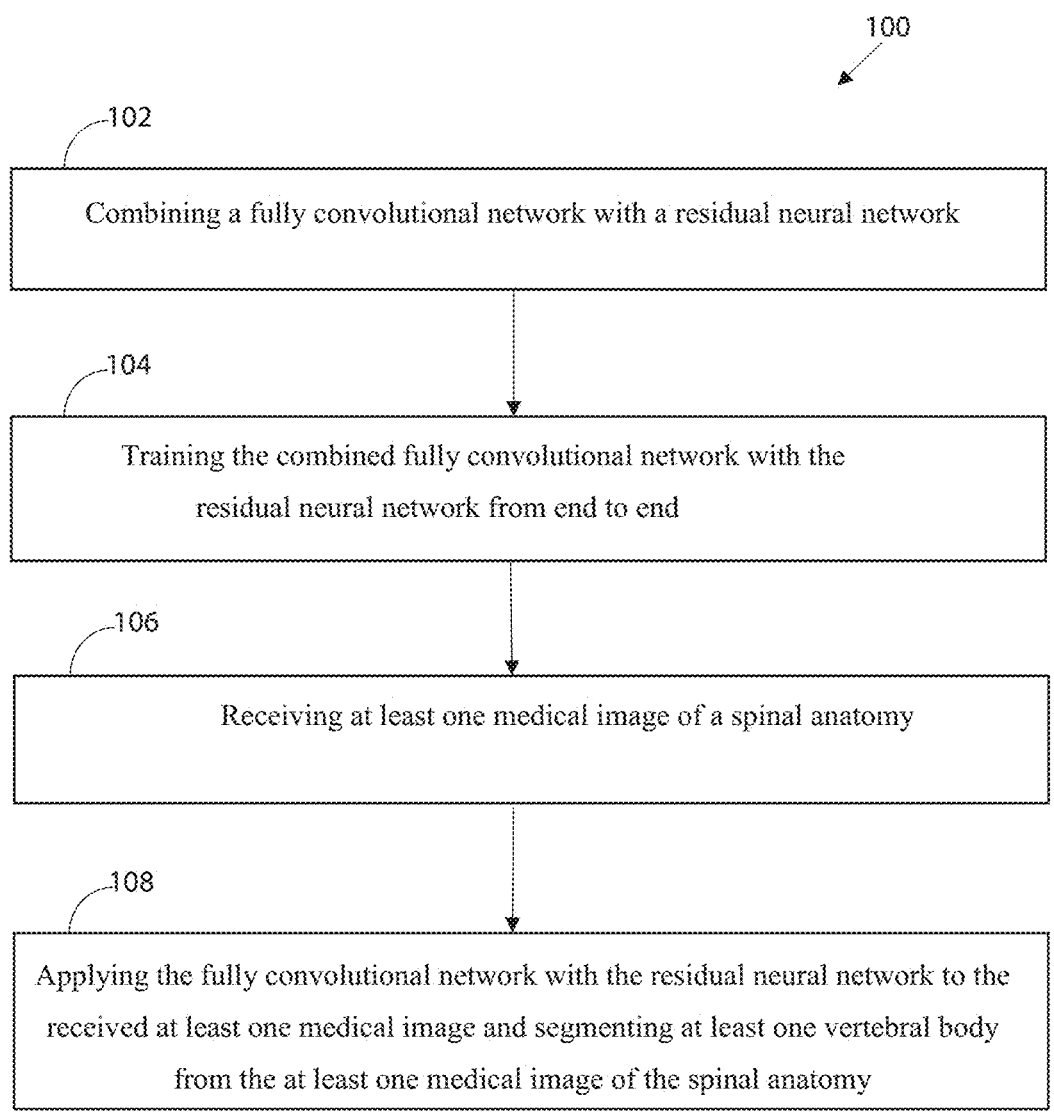
FIG. 1 depicts an example method for intervertebral disc modeling, according to an embodiment of the present disclosure.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The methods disclosed herein provide improvements to an automated vertebral body segmentation method based on tandem convolutional neural networks that learn the appearance of vertebral bodies and pedicles from a training set of magnetic resonance images. In one example, once the segmentation is performed, the vertebral levels are identified automatically. In another example, once the segmentation is performed, the vertebral levels are extracted from the images by an algorithm based on connected components. In another example, intervertebral disc meshes are modeled based on the endplates of the vertebral bodies adjacent the disc to be modeled.

Referring now to the figures, FIG. 1 is flow diagram of an example method for intervertebral disc modeling, in accordance with at least one embodiment described herein. Although the blocks in each figure are illustrated in a sequential order, the blocks my in some instances be performed in parallel, and/or in a different order than those described therein. Also, the various blocks may be combined into fewer blocks, divided into additional blocks, and/or removed based upon the desired implementation.

As shown by block 102, the method 100 includes combining a fully convolutional network (FCN) with a residual neural network (ResNet). In one example, image datasets acquired by various image scanners may lead to different data distributions from one subject to another. This may present a challenge when training a network. In order to overcome this challenge and prior to designing the fully convolutional network, a bias field correction and resampling to isotropic voxel is performed on the image datasets. According to an exemplary embodiment, a three-dimensional anisotropic diffusion filter is applied to smoothen the images. Further, the fully convolutional network is designed to make the intensity distribution of all the input images similar to each other.

As shown by block 104, the method 100 also includes training the combined fully convolutional network with the residual neural network from end to end. In one example, the residual neural network produces a 512×512 output showing a predicted probability value for each pixel based on a two-dimensional slice of size 512×512. In one embodiment, the residual neural network contains a down-sampling and up-sampling process as shown in FIG. 2. In this embodiment, the down-sampling process of the residual neural network architecture includes a convolution layer with kernel size three, two simple blocks, and three basic blocks. These layers are followed by a bottleneck across layer. The up-sampling process is followed by a 1×1 convolutional classifier.

In one example, the network is trained using a gradient descent optimization algorithm. For example, the network is trained using RMSprop gradient descent optimization algorithm with decay set to 0.001. In this example, the initial learning rate is set as 0.001 and dropped to 0.0001 after two hundred epochs. In one example, a three-dimensional fully connected conditional random field is applied on the residual neural network output to further refine the segmentation result of the residual neural network. The designed fully convolutional network and the residual neural network are thereby trained end to end.

As shown by block 106, the method 100 also includes receiving at least one medical image of a spinal anatomy. In one example, the medical image is a magnetic resonance image that has been taken of the relevant anatomy prior to a surgical procedure.

As shown by block 108, the method 100 also includes applying the fully convolutional network with the residual neural network to the received at least one medical image and segmenting at least one vertebral body from the at least one medical image of the spinal anatomy. In one example, given the segmented vertebral bodies, the vertebral levels are labeled semi-automatically. For example, a user indicates the level of the L5 vertebra on the segmented magnetic resonance image. In this example, a three-dimensional connected component extraction algorithm is applied to label different vertebral regions. In one example, the isolated components smaller than a predetermined threshold are removed. In this example, a discrete marching cube algorithm is applied on each component, followed by a mesh smoothing process using a windowed sampling function applied in the frequency domain. This is implemented as an interpolation kernel performed on each voxel. Further, depending on what level has been defined by the user as the lower most vertebra, the remaining vertebrae are labeled in sequential order.

In one embodiment, once the three-dimensional vertebral surfaces are extracted from the segmented vertebral bodies, an intervertebral disc mesh is modeled based on the endplates of the lower and superior vertebrae. By way of example, given the inferior endplate of a top vertebra and the superior endplate of an adjacent lower vertebra, the normals at each point of the meshes are computed, which generates normals for a polygon mesh. In one example, the inferior endplate of the top vertebra is clipped by selecting the points with the normal values less than a predetermined threshold. In this example, the superior endplate of the lower vertebra is clipped by selecting the points with normal values larger than the same predetermined threshold. By way of example, this is done by clipping the adjacent plane, followed by small isolated regions removed by filtering out the larger connected components of the mesh. In one scenario, the Gaussian curvature is computed using an anisotropic curvature filtering technique, which helps to remove outlier curvature values from the two plates. In this scenario, a Laplacian mesh smoothing with fifteen iterations and predetermined relaxation factor is applied on the top vertebra and the lower vertebra to remove endplate irregularities. Further, the resulting smoothed endplates are connected using a Poisson surface reconstruction algorithm.

The flow diagram of FIG. 1 shows the functionality and operation of one possible implementation of the present embodiment. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include non-transitory computer-readable media that stores data for short periods of time, such as register memory, processor cache, or Random Access Memory (RAM), and/or persistent long term storage, such as read only memory (ROM), optical or magnetic disks, or compact-disc read only memory (CD-ROM), for example. The computer readable media may be able, or include, any other volatile or non-volatile storage systems. The computer readable medium may be considered a computer readable storage medium, a tangible storage device, or other article of manufacture, for example.

Alternatively, each block in FIG. 1 may represent circuitry that is wired to perform the specific logical functions in the process. An illustrative method, such as the one shown in FIG. 1, may be carried out in whole in or in part by a component or components in the cloud. However, it should be understood that the example methods may instead be carried out by other entities or combinations of entities (i.e., by other computing devices and/or combination of computer devices), without departing from the scope of the invention. For example, functions of the method of FIG. 1 may be fully performed by a computing device (or components of a computing device such as one or more processors), or may be distributed across multiple components of the computing device, across multiple computing devices, and/or across a server.

Figure 3:
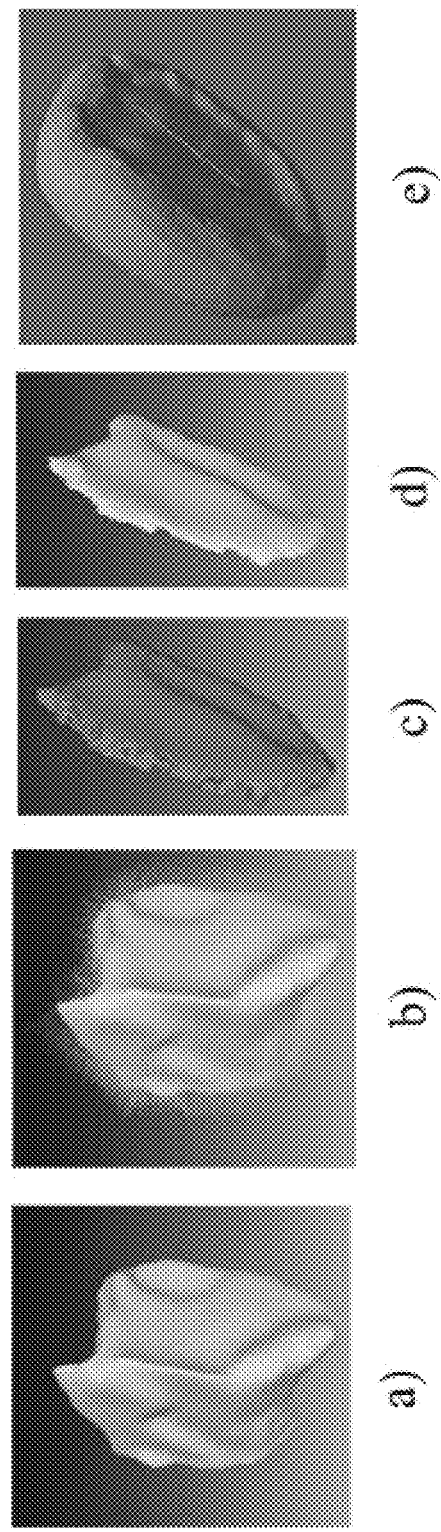
FIG. 3 depicts an example disc surface modeling framework, according to an embodiment of the present disclosure.

FIG. 3 is an example illustration of a disc surface modeling framework according to an embodiment of the present disclosure. As shown in FIG. 3, image A depicts an example top vertebra model. Image B depicts an example of how the facet normals are computed. Image C is an example depiction of a clipped endplate and computed Gaussian curvatures. Image D depicts a final clipped endplate. Image E depicts a disc surface reconstruction between the top and the lower clipped endplates.

Figure 4:
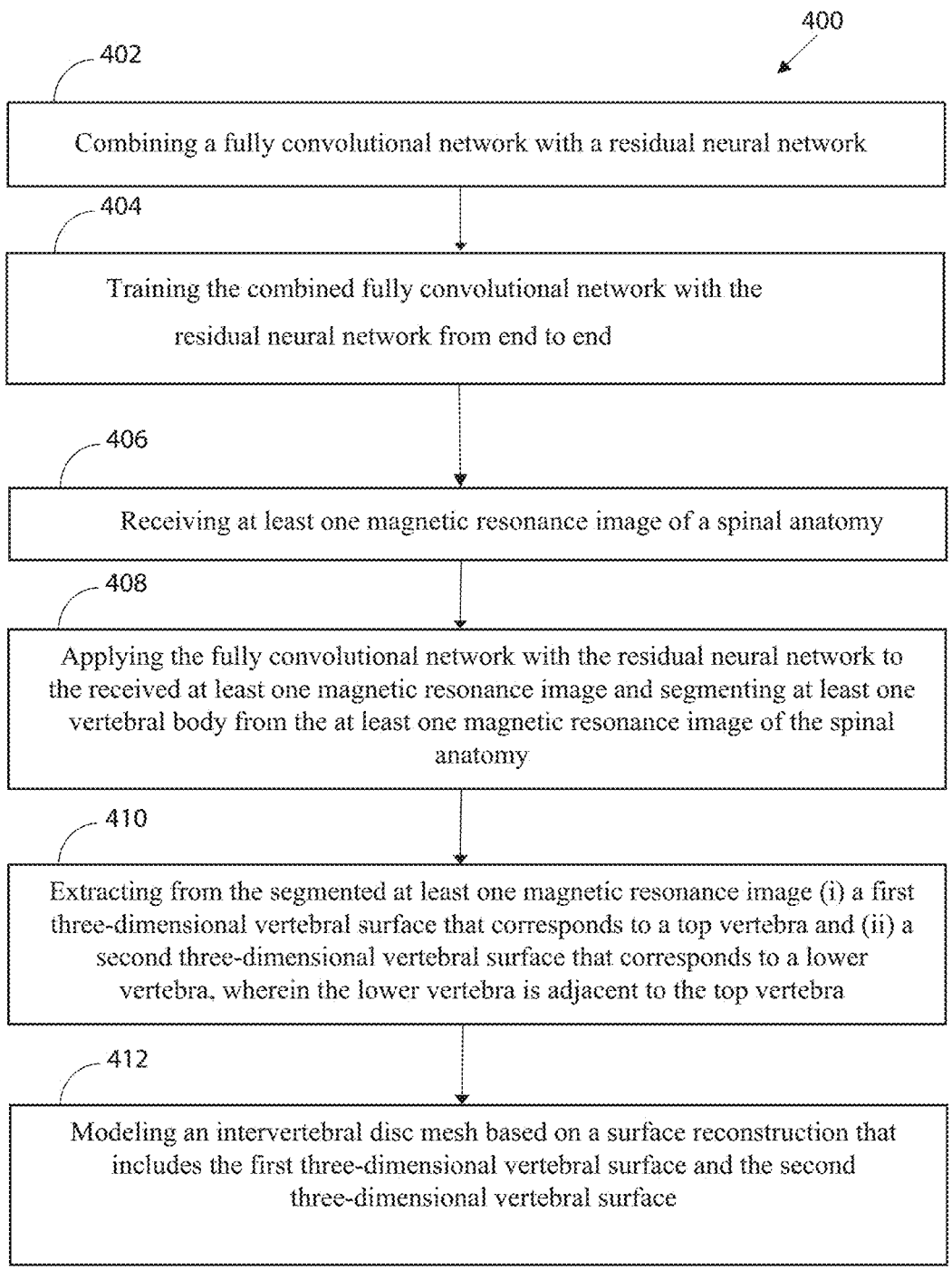
FIG. 4 depicts another example method for intervertebral disc modeling, according to an embodiment of the present disclosure.

FIG. 4 is flow diagram of an example method for intervertebral disc modeling, in accordance with at least one embodiment described herein. Although the blocks in each figure are illustrated in a sequential order, the blocks my in some instances be performed in parallel, and/or in a different order than those described therein. Also, the various blocks may be combined into fewer blocks, divided into additional blocks, and/or removed based upon the desired implementation.

As shown by block 402, the method 400 includes combining a fully convolutional network (FCN) with a residual neural network (ResNet).

As shown by block 404, the method 400 also includes training the combined fully convolutional network with the residual neural network from end to end.

As shown by block 406, the method 400 also includes receiving at least one magnetic resonance image of a spinal anatomy.

As shown by block 408, the method 400 also includes receiving at least one magnetic resonance image of a spinal anatomy applying the fully convolutional network with the residual neural network to the received at least one magnetic resonance image and segmenting at least one vertebral body from the at least one magnetic resonance image of the spinal anatomy.

As shown by block 410, the method 400 also includes extracting from the segmented at least one magnetic resonance image (i) a first three-dimensional vertebral surface that corresponds to a top vertebra and (ii) a second three-dimensional vertebral surface that corresponds to a lower vertebra, wherein the lower vertebra is adjacent to the top vertebra.

As shown by block 412, the method 400 also includes modeling an intervertebral disc mesh based on a surface reconstruction that includes the first three-dimensional vertebral surface and the second three-dimensional vertebral surface.

EXAMPLE 1

In one example, the performance of the approach described herein was performed on two publicly available datasets. The first dataset includes twenty-three subjects with T2-w turbo spin-echo three-dimensional magnetic resonance images of the lower spine. The images were acquired with a 1.5 T Siemens scanner and resampled to a voxel size of 2×1.25×1.25 mm○3. For each vertebral body from T11 to L5, a ground truth manual segmentation was available. In order to test the performance of the designed automatic segmentation method on images from different scanners, a second public dataset of lower spine from SpineWeb was also used. The second dataset includes T2-w MRI and CT scans for twenty cases with different dimensions, voxel spacing, and intensity ranges. For both datasets, manual annotations on vertebral bodies and pedicles was performed.

To increase the size of the dataset, the train datasets were augmented using random flipping (horizontal and vertical), sheering (with maximal range of 0.41), rotations (with maximal range of 10), random cropping (256×256), and spline warping. The spine warping was generated using random displacement vectors on a coarse 3×3 grid. The displacements were sampled from a Gaussian distribution with twenty pixels standard deviation. Per-pixel displacements are then computed using bicubic interpolation.

The vertebral body segmentation evaluation was compared between 2DCNN, 3DCNN, and a standard ResNet, and split the dataset into 5-fold cross-validation. To create a separate validation set, 20% of the data volumes were left out. To implement the tandem deep neural networks, the Keras and Theano libraries were used. For performance validation, the manual segmentations available on the datasets were considered as ground truth. Further, estimations were performed on how close the results from the proposed method were to the ground truth annotations. Dice coefficient, which indicates the amount of volume overlap between the automatically segmented structures and the corresponding manually annotated ones were also computed. In additional, the contour mean distance (CMD) and Hausdorff distance (HD) were also calculated as the average and maximum distance between ground truth and automatic segmentation, respectively.

Finally, in order to compare the MRI automatic segmentation result to CT ground truth segmentations, the proposed output was registered into corresponding CT image space on 20 patients with CT/MRI available. In some cases, MRI scans contained more vertebral levels compared to CT, therefore the extra labels were removed from the ResNet's ouptut.

While the inventive features described herein have been described in terms of a preferred embodiment for achieving the objectives, it will be appreciated by those skilled in the art that variations may be accomplished in view of those teachings without deviating from the spirit or scope of the invention.

What is claimed is:

1. A non-transitory computer readable medium having instructions stored thereon that, when executed by one or more processors, cause the one or more processors to:
   receive at least one medical image of a spinal anatomy;
   segment at least one vertebral body from the at least one medical image of the spinal anatomy;
   extract one or more three-dimensional vertebral surfaces from the segmented at least one medical image, wherein the extracted one or more three-dimensional vertebral surfaces comprises a first surface that corresponds to an inferior endplate of a top vertebra and a second surface that corresponds to a superior endplate of a lower vertebra, wherein the lower vertebra is adjacent to the top vertebra;
   model an intervertebral disc mesh based on the extracted one or more three-dimensional vertebral surfaces that correspond to the inferior endplate of the top vertebra and the superior endplate of the lower vertebra;
   determine normal vectors at one or more points along the first surface and the second surface;
   clip the first surface and the second surface according to a predetermined threshold that corresponds to a value associated with the normal vectors; and
   model the intervertebral disc mesh based on a surface reconstruction that includes the clipped first surface and the clipped second surface.

2. The non-transitory computer readable medium of claim 1, wherein the instructions further cause the one or more processors to:
   apply a down-sampling and up-sampling process to the medical image.

3. The non-transitory computer readable medium of claim 1, wherein the instructions further cause the one or more processors to:
   apply a trained machine learning system that includes a convolutional neural network to process the at least one medical image.

4. The non-transitory computer readable medium of claim 1, wherein the instructions further cause the one or more processors to:
   apply a three-dimensional fully connected conditional random field on an output of a residual neural network.

5. The non-transitory computer readable medium of claim 1, wherein the instructions further cause the one or more processors to:
   receive an identification of a vertebral level on the segmented at least one medical image; and
   determine identification of one or more additional vertebral levels based on the identification.

6. The non-transitory computer readable medium of claim 5, wherein to determine identification of one or more levels includes to:
   apply a three-dimensional connected component extraction algorithm.

7. The non-transitory computer readable medium of claim 5, wherein the instructions further cause the one or more processors to:

receive a selection of one or more determined vertebral levels;

wherein to extract one or more three-dimensional vertebral surfaces from the segmented at least one medical image is based on the received selection.

8. The non-transitory computer readable medium of claim 1, wherein to segment includes to:

apply a trained machine learning system to the received at least one medical image.

9. The non-transitory computer readable medium of claim 1, wherein the instructions further cause the one or more processors to:

smooth the at least one medical image with a three-dimensional anisotropic diffusion filter.

10. The non-transitory computer readable medium of claim 1, wherein the at least one medical image of the spinal anatomy includes a plurality of images; and wherein the instructions further cause the one or more processors to:

modify an intensity distribution of the plurality of images.

11. The non-transitory computer readable medium of claim 1, wherein the instructions further cause the one or more processors to:

apply a bias field correction and resampling to isotropic voxel to the at least one medical image.

12. The non-transitory computer readable medium of claim 1, wherein the instructions further cause the one or more processors to:

apply a discrete marching cube algorithm to one or more components, followed by a mesh smoothing process using a windowed sampling function applied in a frequency domain.

13. A method for spinal anatomy segmentation, comprising:

receiving at least one magnetic resonance image of a spinal anatomy;

segmenting at least one vertebral body from the at least one magnetic resonance image of the spinal anatomy, wherein the segmenting includes applying a trained machine learning system to the received at least one magnetic resonance image;

extracting from the segmented at least one magnetic resonance image:

a first three-dimensional vertebral surface that corresponds to an inferior endplate of a top vertebra; and a second three-dimensional vertebral surface that corresponds to a superior endplate of a lower vertebra adjacent to the top vertebra;

modeling an intervertebral disc mesh based on a surface reconstruction that includes the first three-dimensional vertebral surface corresponding to the inferior endplate of the top vertebra and the second three-dimensional vertebral surface corresponding to the superior endplate of the lower vertebra;

clipping the first three-dimensional vertebral surface that corresponds to the inferior endplate of the top vertebra according to a predetermined threshold;

clipping the second three-dimensional vertebral surface that corresponds to the superior endplate of the lower vertebra according to the predetermined threshold; and modelling the intervertebral disc mesh based on a surface reconstruction that includes the clipped first three-dimensional vertebral surface and the clipped second three-dimensional vertebral surface.

14. The method of claim 13, wherein the method further includes:

removing one or more vertebral surface irregularities from the interior endplate and the superior endplate prior to modeling the intervertebral disc mesh.

15. The method of claim 14, wherein the removing of the one or more vertebral surface irregularities includes applying a Laplacian mesh smoothing process.

16. The method of claim 14, further comprising connecting the first and second three-dimensional vertebral surfaces using a Poisson surface reconstruction algorithm.

17. A system for spinal anatomy segmentation, the system comprising:

one or more processors;

a computer readable medium having instructions stored thereon that, when executed by the one or more processors cause the one or more processors to:

receive at least one image of a spinal anatomy;

apply a trained machine learning system to the received at least one image and segment at least two vertebral bodies from the at least one image of the spinal anatomy;

extract one or more three-dimensional vertebral surfaces from the segmented at least one image including:

a first three-dimensional vertebral surface that corresponds to an inferior vertebral endplate of a top vertebra; and a second three-dimensional vertebral surface that corresponds to a superior vertebral endplate of a lower vertebra adjacent to the top vertebra;

model an intervertebral disc mesh based on a surface reconstruction that includes the first three-dimensional vertebral surface corresponds to the inferior vertebral endplate of the top vertebra and the second three-dimensional vertebral surface corresponds to the superior vertebral endplate of the lower vertebra;

clip the first three-dimensional vertebral surface that corresponds to the inferior endplate of the top vertebra according to a predetermined threshold;

clip the second three-dimensional vertebral surface that corresponds to the superior endplate of the lower vertebra according to the predetermined threshold; and model the intervertebral disc mesh based on a surface reconstruction that includes the clipped first three-dimensional vertebral surface and the clipped second three-dimensional vertebral surface.

* * * * *